United States Patent
Malm

(10) Patent No.: US 8,784,331 B2
(45) Date of Patent: Jul. 22, 2014

(54) METHOD AND DEVICE FOR DETERMINING THE HYDRODYNAMICS OF THE CEREBROSPINAL FLUID SYSTEM

(75) Inventor: Jan Malm, Umeå (SE)

(73) Assignee: Likvor AB, Umea (SE)

( * ) Notice: Subject to any disclaimer, the term of this patent is extended or adjusted under 35 U.S.C. 154(b) by 1149 days.

(21) Appl. No.: 11/885,137

(22) PCT Filed: Feb. 27, 2006

(86) PCT No.: PCT/SE2006/000252
§ 371 (c)(1), (2), (4) Date: Jul. 17, 2008

(87) PCT Pub. No.: WO2006/091164
PCT Pub. Date: Aug. 31, 2006

(65) Prior Publication Data
US 2008/0306403 A1    Dec. 11, 2008

(30) Foreign Application Priority Data
Feb. 28, 2005 (SE) .................... 0500481

(51) Int. Cl.
*A61B 5/03* (2006.01)
*A61M 5/00* (2006.01)

(52) U.S. Cl.
USPC ............... 600/561; 600/485; 604/9

(58) Field of Classification Search
USPC ............ 600/561, 300, 301, 485, 486; 604/9
See application file for complete search history.

(56) References Cited

U.S. PATENT DOCUMENTS

| | | | | |
|---|---|---|---|---|
| 4,114,603 A | | 9/1978 | Wilkinson | |
| 4,672,974 A | * | 6/1987 | Lee | 600/486 |
| 4,869,265 A | * | 9/1989 | McEwen | 600/587 |
| 4,949,723 A | * | 8/1990 | Wallace et al. | 600/485 |
| 5,355,880 A | * | 10/1994 | Thomas et al. | 600/326 |
| 5,752,520 A | * | 5/1998 | Bisnaire et al. | 600/561 |
| 6,675,031 B1 | * | 1/2004 | Porges et al. | 600/322 |
| 7,635,338 B2 | * | 12/2009 | Eide | 600/485 |
| 2003/0100845 A1 | * | 5/2003 | Eide | 600/561 |

* cited by examiner

FOREIGN PATENT DOCUMENTS

| JP | 11-299742 A | 11/1999 |
|---|---|---|
| WO | WO 02/03860 A1 | 1/2002 |

OTHER PUBLICATIONS

Andersson, Nina et al. "Assessment of cerebrospinal fluid outflow conductance using constant-pressure infusion—a method with real time estimation of reliability." Nov. 22, 2005. Institute of Physics Publishing. Physiological Measurement. vol. 26. p. 1137-48.*

*Primary Examiner* — Max Hindenburg
*Assistant Examiner* — John Pani
(74) *Attorney, Agent, or Firm* — Lynn E. Barber

(57) ABSTRACT

The present invention relates to a method and a device for determining the hydro-dynamic properties of the fluid system surrounding the brain and the spinal cord, the so called cerebrospinal fluid system, whereby the method comprises continuous pressure measurement through a fluid contact passage and active infusion of artificial cerebrospinal fluid through another fluid contact passage to a number of pressure-flow levels, and analysis of the connections between the measured pressures and flows. The method uses an adaptive way of procedure which on each pressure-flow level takes account for the measure time and the patient's fluctuations in physiologic signals for calculating in real time when the relation between the measure time and measure accuracy in pressure and flow on the actual pressure-flow level is sufficient and at an optimum, whereupon the investigation or examination is automatically proceeding to the next level according to a predetermined protocol. In this way, the method gives rise to an investigation with measurements having sufficient pressure and flow information on each level, which forms a base for determination in a correct manner, with an uncertainty estimate, of the patient's hydrodynamic parameters. The device comprises a hose pump (1) for infusion of artificial cerebrospinal fluid in a bottle or bag (2), a standardized hose set including a pump hose (3) and pressure transducers (4) for continuous registration of the intracranial pressure, an invasive contact object (5) for creating fluid contact with the cerebrospinal fluid system and consisting of needles or a catheter, as well as a computer (12) with software for computerized collection and analysis as well as control of pump speed. The device uses a computerized implementation of the above-mentioned adaptive method in order to systematically and safely carry through a standardized protocol which generates pressure and flow information which the software of the measure system then uses for determining in real time and with an uncertainty estimate, the hydrodynamic parameters of the system.

2 Claims, 1 Drawing Sheet

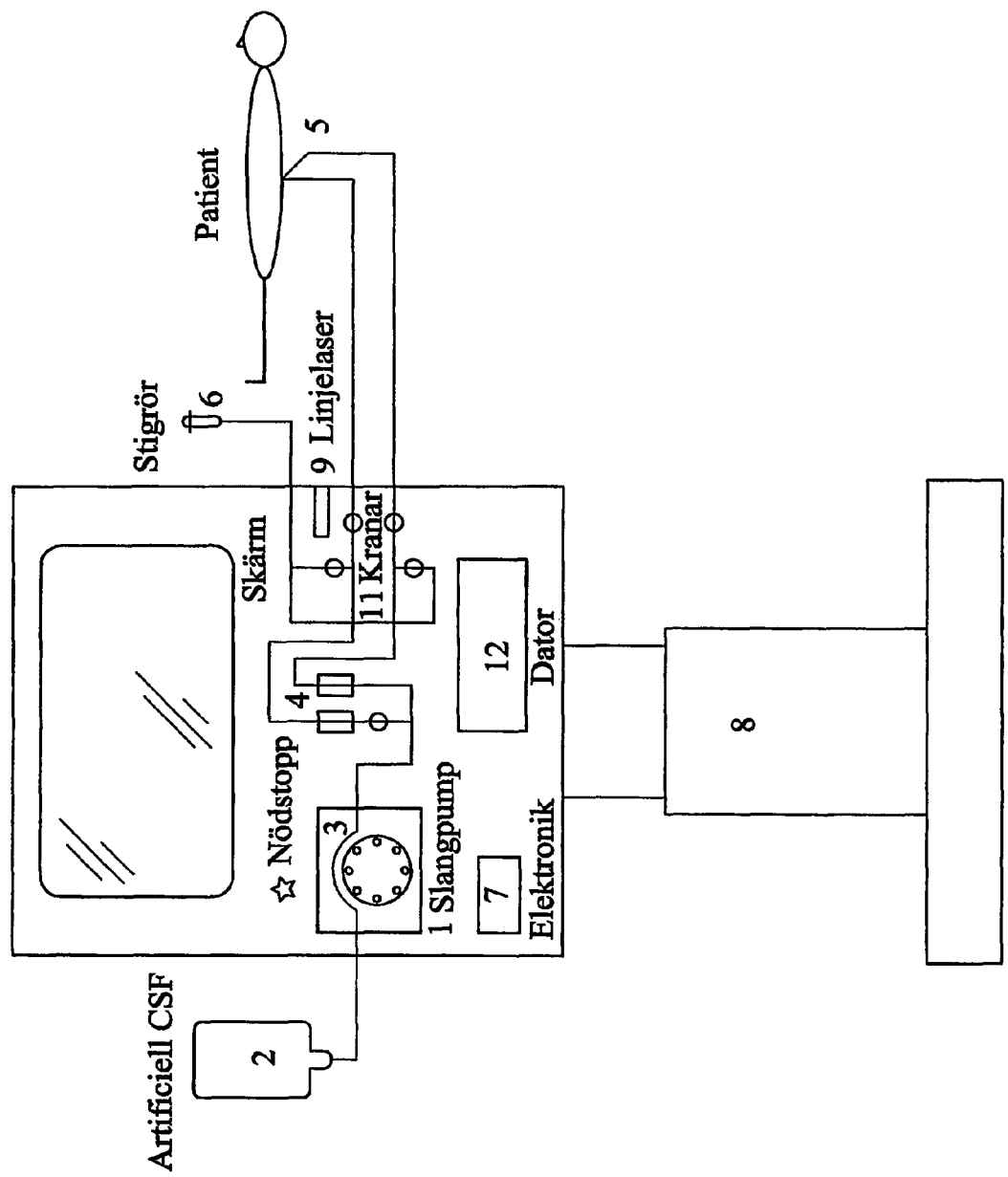

METHOD AND DEVICE FOR DETERMINING THE HYDRODYNAMICS OF THE CEREBROSPINAL FLUID SYSTEM

FIELD OF THE INVENTION

The present invention relates to a method and a device for determining the hydrodynamic properties of the fluid system surrounding the brain and spinal cord. Thus, by means of the invention, one can show or indicate disturbances or divergences in these hydrodynamic properties due to e.g. hydrocephalus at patients and examine whether the shunt system of the patient is functioning.

BACKGROUND OF THE INVENTION

The brain and the spinal cord are surrounded by cerebrospinal fluid (CSF), the primary purpose of which is to function as a support: the brain of a grown-up person weighs about 1.5 kg—placed in water the weight is about 50 g. CSF is formed in the cavities of the brain, the so called ventricles. From here, CSF is flowing through a passage system and out over the surface of the brain and spinal cord. Drainage occurs through special structures, so called arachnoidal villi, in connection with the venous blood vessels. The CSF system forms a fluid system with patient-dependent hydrodynamic properties.

There are several diseases which can affect the CSF system and a reduced drainage of CSF or an increased pressure inside the cranial cavity (intracranial pressure, ICP) can give rise to a number of symptoms. Hydrocephalus means that the ventricles of the brain increase in size and thereby, the amount of fluid therein. The symptoms of the patient can vary, sometimes ICP increases and the patient is suffering from headache and reduced wakefulness. A more common variant, the so called adult hydrocephalus syndrome (AHS) or normal pressure hydrocephalus (NPH), means that the patient suffers from a triade of symptoms with walking disorders, memory disorders and urinary incontinence.

Hydrocephalus can be treated with a CSF shunt. Every year, about 70000 shunts are implanted in the west, which makes it one of the most common neurosurgical operations. Therefore, it is important to find selection methods where the probability for a successful result is high. Such a selection method is built, inter alia, on determining the hydrodynamic properties of the CSF system of the patient.

The base for determining the hydrodynamic properties of the CSF system is built on insertion of needles, lumbarly or cranially, such that contact with the fluid system is obtained. Then, the intracranial pressure (ICP) is measured during an active infusion of artificial CSF. The connection between the infusion flow and ICP, as a function of time, is analyzed by means of a physiological model which may include system-defining parameters such as CSF production, outflow resistance, compliance, venous pressure etc. Thus, from the measurement, the patient values of these parameters are estimated. It is particularly the outflow resistance which today is used for determining the hydrodynamic properties of the CSF system.

A method commonly used today on many hospitals, makes use of an infusion pump with constant infusion rate which through a needle is connected lumbarly to the spinal cord canal. A resting pressure prior to start of the pump, a dynamic process with a pressure increase during 5 to 10 minutes after pump start and a sequence with equilibrium pressure during infusion are registered. The outflow resistance is determined based on the two equilibrium levels and compliance from the process of increase. Drawbacks with the method are that the precision of a determination based on two points as well as determination of a dynamic parameter in such a short time as 5 to 10 minutes is low and no statistic uncertainties are recorded. The method is manual and has no security connections between pump and pressure measurement and is therefore regarded as technically difficult to carry through as well as for final analysis.

A prior prototype of the present method and device was based on a feed-back system with two lumbarly located standard needles. ICP is registered through one needle and then, the flow is guided through the other needle by a control system the object of which is to keep the pressure on constant levels. The resting pressure is first determined and then, three to five different constant pressure levels are set and the flow for each level determined. Linear regression between the pressure and flow plots is used for determining the outflow resistance. This method is considered more accurate than the first, but has also no uncertainty analysis, utilizes a manual protocol and is technically demanding with advanced pressure and flow calibrations and manual final analysis. This method further requires a specially trained operator capable of determining by visual estimation when one shall go from one pressure level to another in the protocol.

A problem in connection with determining the hydrodynamic parameters of the CSF system is the extensive natural physiologic fluctuations of the intracranial pressure and the volume of the system. The fluctuations depend particularly on rhythmic fluctuations of the blood volume in the brain related to the heart rhythm and the breathing rhythm etc. These fluctuations might render it necessary to measure very small outflow volumes in an environment with extensive inner volume fluctuations (very low signal/noise relation). The physiologic fluctuations differ extensively from patient to patient. The present methods for measuring the CSF dynamics disregard variations between patients.

SUMMARY OF THE INVENTION

Consequently, it is an object of the present invention to reduce or eliminate the above-mentioned drawbacks of prior art methods and devices for measuring and determining the hydrodynamic properties of the CSF system.

This is arrived at by means of a method and a device based on infusion technique and including the measures and features respectively, defined in the claims.

BRIEF DESCRIPTION OF THE DRAWING

These and further characterizing measures and features of the invention as well as advantages therewith will be further described below with reference to the accompanying drawing.

FIG. 1 schematically illustrates a device according to the invention for carrying through the method according to the invention.

DESCRIPTION OF EXAMPLE EMBODIMENT

According to the invention, a method and a device for an adaptive measure and analysis system are proposed for measuring pressure and controlled infusion to a CSF system for determining the hydrodynamic properties thereof. The method presents a number of new technical solutions compared to the prior prototype and previously described methods for, in connection with said determination, simplify the operation, increase safety, permit standardization and automatization by adaptive control of protocols based on continuous statistic analysis, and thereby obtain a method which is safer for the patient and with improved indication of disturbances or disorders in the hydrodynamic properties. It has been noticed that the system can reproducibly measure the hydrodynamic parameters in a manner previously not possible.

The idea with the method according to the invention is to use an adaptive method for systematically carrying through a predetermined protocol which generates or provides pressure and flow information that is used for determining, with an uncertainty estimate, the hydrodynamic parameters of the patient. The protocol can be based on a number of pressure-flow levels which are created by constant flow rates, flow rates that are varied according to a specific pattern, which generates a pressure fluctuation pattern, or adjustment of the flow while maintaining predetermined pressure levels. The method can use predetermined time intervals for each pressure-flow level and automatically proceed to the next level when sufficient accumulated time with accepted data has been collected. This embodiment provides standardized investigations with regard to the measure time which can be analyzed and measurements comparable therewith. In a second embodiment, it is possible to use signal analytic real-time methods, such as confidence intervals of a distribution, in order to estimate the accuracy or precision in the pressure and flow determined under each level and use this information to adaptively control when the investigation shall proceed to the next pressure-flow level. In a third embodiment, infusion is applied with cyclic variation in flow rate according to a predetermined pattern, superposed on one or more basic flow levels, and so, the response of pressure data is analyzed starting from or on the basis of a hydrodynamic model, with e.g. adaptive model-characterizing methods, such that values and the accuracy in estimated values for the patient's outflow resistance, resting pressure and compliance are continuously updated, whereupon the method is automatically proceeding to the next basic flow level when sufficient accuracy or precision has been obtained on one level.

Sufficient accuracy in accordance with the method according to the invention is obtained or reached when a certain threshold value for a presented statistic parameter reflecting the accuracy (i.e. how accurate or precise pressure and flow have been determined at each time) on the level in question is underpassed by the accuracy measured in real time (i.e. by the measured value of said parameter). According to the invention, the parameters measured when the measure accuracy shall be estimated are preferably partly for the net flow on each level (95% confidence interval for the slope of the linear regression of infusion volume as a function of time on each level), partly the over-arching accuracy for the entire investigation (estimate of 95% confidence interval for the slope coefficient between pressure levels and net flows on these levels), and a threshold value for the parameter in question is determined for obtaining or reaching sufficient measuring accuracy also for patients with large physiologic fluctuations.

Embodiment two and three above provide for an optimized measure accuracy per investigation time. In order to reach the same precision, a patient with large physiologic fluctuations on a certain level will consequently be examined for a longer time period on this level in order to reach or obtain sufficient precision, than a patient having small physiologic fluctuations, since the distribution of pressure and flow data in said former case is larger, which results in that the statistic certainty becomes less and that it therefore will take a longer time to underpass the abovementioned certain threshold value.

This means that the precision for given parameters becomes sufficient on all levels. Adaptive control in this way provides for infusion tests which are adapted to the patients and therefore also comparable to each other. Patients with small fluctuations get a short examination time and patients with large fluctuations require longer examination time for reaching a corresponding precision in the determined hydrodynamic parameters (outflow resistance, compliance etc.). Fluctuations depending on known reasons, such as the patient moving or talking, can also be indirectly eliminated by the operator noting the incident. Another example of reasons when portions of measured data can be eliminated, is pump stops initiated by a built-in safety system. In order to optimize the investigation or examination in view of measure time and accuracy, one can use a combination of the two methods. Thereby, one can let the measure system, when deciding to proceed to the next level, to use combined criteria for measure time, measure accuracy in pressure and flow, and change per time unit in measure accuracy in pressure and flow. In all methods there is also a final statistic estimation of the achieved or obtained precision in the determined parameters such that the physician can evaluate the importance of the measurement results in connection with the indication of the disturbance or disorder in the hydrodynamic properties.

Thus, by adaptive method is meant that the investigation or examination is carried through in a manner such that the size and accuracy in determined parameters such as pressure and flow values for different pressure-flow levels and thereby also size and accuracy in determining the patient's hydrodynamic properties such as outflow resistance, compliance, resting pressure and CSF generating rate, are continuously estimated during the investigation and used for controlling the measure protocol so that an optimized measure accuracy per investigation or examination time is obtained. The feedback connection to protocol control of actual result accuracy during the measurement, is at the same time a guarantee for that sufficient accuracy has been obtained before the investigation is finished.

A device for carrying through the method according to the invention for measuring the hydrodynamic properties of the CSF system, is shown in the drawing. The device comprises a hose pump 1 for infusion of artificial CSF from a container 2, e.g. a bottle or bag therefor. Said artificial CSF is fed by the pump 1 from said container 2 through pump hoses 3 and pressure transducers 4 for continuous registration of the intracranial pressure to a contact object 5 for defining or establishing lumbarly, through the spinal canal, double fluid contacts with the CSF system. Said contact object 5 consists of, as in the previous model, two needles or, as in the new embodiment, of one needle or catheter with double lumen. Artificial CSF or similar is by means of the pump 1 pumped through one passage into or out of the CSF system. By means of the standardized pressure transducers 4 the pressure is measured through both passages.

In the embodiment with two needles, needles are preferably used which according to the invention have a number of additional holes drilled on the sides at the point of the needles. In this way, a better contact with the CSF system is obtained and it is avoided that pump needles are obstructed when soft tissue in the spinal canal is drawn towards the needle when pumping fluid out of the system.

The advantage with the embodiment with the new double lumen needle alternatively double lumen catheter is that it is enough with one input passage. Regarding the solution with the double lumen catheter, the investigation or examination can be carried through even in a normal hospital bed. Needles require a special bed with a hole in the bottom through which the needles can be inserted into the spinal canal.

The catheter solution and the pressure measuring function of the equipment also renders it possible, after the infusion test is finished and without any new surgical operation, to carry through other predictive tests for hydrocephalus investigation, e.g. a long-term measurement or a so called tapp test.

The device according to the invention further comprises a computer 12 with software for computerized collection and analysis as well as control of the pump speed. A calculation unit, forming part of the software of the computer, is controlled by said software to use the adaptive method which at each pressure-flow level considers the time of measure and the patient's fluctuations in physiologic signals for calculating, in real time, when the relation between measure time and measure accuracy in pressure and flow on the actual level is sufficient. The software is designed and constitute means for, when said relation between measure time and measure accuracy on the actual level is sufficient, initiating the next pressure-flow level according to a predetermined protocol. Furthermore, the software is designed for real-time analysis, i.e. constitutes means for real-time analysis for, from the pressure-flow information from the investigation, determining and giving an account of the patient's hydrodynamic parameters with an uncertainty estimate.

The calculation unit can also be designed to, by means of signal analytic methods as defined above, in real time estimate the accuracy in the determined pressure and flow on each pressure-flow level, and by means of this information adaptively control when it is time to proceed to the next level, or to carry through at each pressure-flow level a measurement during a predetermined time interval.

The pump 1 is controlled to apply infusion with cyclic variation in flow velocity according to a given pattern, superposed on one or more basic flow levels, and the calculation unit is further designed to analyze the response of pressure data emanating from the hydrodynamic model such that values and the accuracy of estimated values for the patient's outflow resistance, resting pressure and compliance are continuously updated, whereupon said software automatically initiates the next basic flow level when sufficient accuracy on one level has been reached.

Said software is further designed to directly eliminate, as defined above, measure intervals with signal variations depending on known circumstances, errors noted by a built-in safety system or incidents registered by the operator.

Said software is also designed to calculate and present a final statistic estimate of the resulting precision in the determined parameters.

The advanced and time consuming calibration routines of the prior system is avoided by using a standardized hose set with the pump hose 3, the statistic variation of which from hose set to hose set is carefully tested. Furthermore, a simple combined calibration test of pressure transducers 4 as well as pump system 1, 3 is carried through prior to each investigation. It consists of a vertically located stand pipe 6, integrated in the hose system, which is automatically filled by the pump 1 to a predetermined volume. The pressure increase due to the increased height of the column is registered by the pressure transducers 4 and automatically controlled in view of given deviation standards. In this manner, the accuracy in flow measurement as well as pressure measurement is tested in an automated procedure.

This type of invasive investigation or examination makes great demands upon security thinking. An active infusion is used for regulating or controlling the intracranial pressure, but if the pressure gets too high or too low, the patient is put in a life-threatening condition. Existing infusion equipment for this type of measurements contains no built-in safety routines, but leaves the entire responsibility to the operator. The present invention includes a plurality of new technical solutions for eliminating generation of injurious pressures due to defects in the hardware and software of the equipment.

One danger is if the software does not operate properly and generates a control signal which is not related to the actual pressure. This is solved by means of a toggle signal between the electronics/hardware 7 and the computer/software 12 of the device controlling that the software operates properly. If the toggle signal is not sent continuously, the pump 1 is stopped by the hardware 7.

Control of that the intracranial pressure is within the allowed range is made internally by the electronics/hardware 7, which otherwise stops the pump 1 and sends an error message to the computer/software 12.

Control of that the intracranial pressure is within the allowed range is alternatively made by the software, whereby the pump 1 is brought to a stop at injurious pressures and an error message is presented.

Control of that the pressure measurement is intact is made by comparing the pressure from the two fluid passages and by controlling that there are pulsations related to the cardiac cycle in the pressure signal. By deviations the pump 1 is stopped.

When measuring a physiologic pressure through fluid hoses, it is important to compensate for static errors generated because of hydrostatic columns in the hoses. This compensation can be done by locating and clearing the pressure transducers 4 at the zero level of the patient (for the intracranial pressure this means at the ear canal). In order to facilitate this level location, the entire apparatus, including the transducers 4, is mounted on an electrically elevated pillar 8. The equipment also includes a horizontally suspended linear laser 9 which generates a horizontal line on a level with the level of the transducers. In this way, the operator can easily compensate for any hydrostatic parts by guiding the pillar 8 such that the line is located at the ear canal of the patient.

In one embodiment a sterilized standardized hose set is used, which includes a pump hose 3 which is adapted to the hose pump 1, two disposable pressure transducers 4, stopcocks 11 and hoses from the CSF container 2 and to patient. Everything is mounted on a plastic sheet for easy mounting on the pillar 9.

In an alternative embodiment the stopcocks are replaced by soft clamp hoses and instead there are solenoid stopcocks 11 on the surface of the apparatus. This will permit complete automatization also of the preparatory work prior to investigation.

The invention claimed is:

1. A device for automatically determining hydrodynamic characteristics of a patient cerebrospinal fluid system, comprising: (a) a hose pump for infusion of artificial cerebrospinal fluid from a container into or out of the patient cerebrospinal fluid system for continuous pressure measurement through a first fluid contact passage and active infusion of artificial cerebrospinal fluid through a second fluid contact passage;
   (b) a pump hose through which the artificial cerebrospinal fluid is fed from the container;
   (c) pressure transducers for continuous measurement of intracranial pressure;
   (d) an invasive contact object, connected to the pump hose, with two lumens for creating fluid contact with the cerebrospinal fluid system; and (e) a computer for control of the hose pump, the computer having software for computerized collection and analysis, and programmed according to a predetermined protocol that generates or provides pressure and flow information and uses the information for determining, with an uncertainty estimate, the hydrodynamic characteristics of the patient, wherein the computer is programmed to initially measure each level of pressure and flow for predetermined time intervals, and to automatically proceed to a next level of pressure and flow based upon a determination by the computer that a sufficient accuracy or precision of the hydrodynamic properties has been obtained.

2. A device for automatically determining hydrodynamic characteristics of a patient cerebrospinal fluid system, comprising: (a) a hose pump for infusion of artificial cerebrospinal fluid from a container into or out of the patient cerebrospinal fluid system for continuous pressure measurement through a first fluid contact passage and active infusion of artificial cerebrospinal fluid through a second fluid contact passage;

(b) a pump hose through which the artificial cerebrospinal fluid is fed from the container;

(c) pressure transducers for continuous measurement of intracranial pressure;

(d) an invasive contact object, connected to the pump hose, with two lumens for creating fluid contact with the cerebrospinal fluid system; and (e) a computer for control of the hose pump, the computer having software for computerized collection and analysis, and programmed according to a predetermined protocol that generates or provides pressure and flow information and uses the information for determining, with an uncertainty estimate, the hydrodynamic characteristics of the patient, wherein the computer is programmed to:

(i) make a determination that a patient has large fluctuations in physiological signal if the computer determines physiological signal fluctuations meet predetermined conditions, and based upon that determination, measure pressure and flow for a first time period of a first length; and (ii) make a determination that a patient has a small fluctuation if the computer determines physiological signal fluctuations do not meet the predetermined conditions, and based upon that determination, measure pressure and flow for a second time period of a second length, where the second length is less than the first length.

* * * * *